United States Patent
Ahn

(10) Patent No.: US 11,529,181 B2
(45) Date of Patent: Dec. 20, 2022

(54) PLASMA SKIN CARE DEVICE

(71) Applicant: AGNES MEDICAL CO., LTD., Seongnam-si (KR)

(72) Inventor: Gunyoung Ahn, Seongnam-si (KR)

(73) Assignee: AGNES MEDICAL CO., LTD., Seongnam-si (KR)

( * ) Notice: Subject to any disclaimer, the term of this patent is extended or adjusted under 35 U.S.C. 154(b) by 413 days.

(21) Appl. No.: 16/837,335

(22) Filed: Apr. 1, 2020

(65) Prior Publication Data
US 2020/0315682 A1 Oct. 8, 2020

(30) Foreign Application Priority Data
Apr. 4, 2019 (KR) .................. 10-2019-0039604

(51) Int. Cl.
*A61B 18/04* (2006.01)
*A61B 18/12* (2006.01)
(Continued)

(52) U.S. Cl.
CPC ........ *A61B 18/042* (2013.01); *A61B 18/1206* (2013.01); *A61N 1/44* (2013.01);
(Continued)

(58) Field of Classification Search
CPC .............. A61B 18/042; A61B 18/1206; A61B 2018/00202; A61B 2018/00291; A61B 2018/00452; A61B 2018/0091; A61B 2018/124; A61B 2218/007; A61B 2018/0016; A61N 1/44; A61N 5/0616;
(Continued)

(56) References Cited

U.S. PATENT DOCUMENTS

2016/0015843 A1* 1/2016 Jang ........................ A61L 9/22
422/123
2016/0331439 A1* 11/2016 Winkelman ............. A61K 8/22
(Continued)

FOREIGN PATENT DOCUMENTS

JP 2014-104194 A 6/2014
KR 2010058090 A * 6/2010
(Continued)

OTHER PUBLICATIONS

Korean Office Action for related KR Application No. 10-2019-0039604 dated Sep. 28, 2020 from Korean Intellectual Property Office.
(Continued)

*Primary Examiner* — Gary Jackson
*Assistant Examiner* — Sebastian X Lukjan
(74) *Attorney, Agent, or Firm* — Paratus Law Group, PLLC

(57) ABSTRACT

Disclosed is a plasma skin care device including a handpiece, an ozone decomposition module, and a suction fan. The handpiece has a plasma generator and discharges plasma in a state in which a front end portion of the plasma generator is adjacent to skin. The ozone decomposition module is configured to receive and decompose ozone, which is generated when the plasma is discharged, from the handpiece. The suction fan is configured to draw the ozone generated in the handpiece to the ozone decomposition module by suction pressure.

13 Claims, 13 Drawing Sheets

(51) Int. Cl.
*A61N 1/44* (2006.01)
*A61B 18/00* (2006.01)
*A61N 5/06* (2006.01)

(52) U.S. Cl.
CPC .............. *A61B 2018/0091* (2013.01); *A61B 2018/00202* (2013.01); *A61B 2018/00291* (2013.01); *A61B 2018/00452* (2013.01); *A61N 5/0616* (2013.01)

(58) Field of Classification Search
CPC ... A61L 9/205; B01D 53/005; B01D 53/8675; H05H 1/24
See application file for complete search history.

(56) References Cited

U.S. PATENT DOCUMENTS

| | | | |
|---|---|---|---|
| 2017/0128127 A1* | 5/2017 | Skalnyi | A61B 18/1485 |
| 2018/0264160 A1* | 9/2018 | Benedek | A61L 2/10 |
| 2019/0046809 A1* | 2/2019 | Kang | H01J 37/32449 |

FOREIGN PATENT DOCUMENTS

| | | | | | |
|---|---|---|---|---|---|
| KR | 10-1076329 B1 | 10/2011 | | | |
| KR | 10-1407090 B1 | 6/2014 | | | |
| KR | 10-1773847 B1 | 9/2017 | | | |
| KR | 10-2018-0041468 A | 4/2018 | | | |
| KR | 10-1859187 B1 | 5/2018 | | | |
| KR | 2018095405 A | * | 8/2018 | ........... | A61B 18/203 |
| KR | 10-2018-0110489 A | 10/2018 | | | |
| WO | WO-2018024909 A1 | * | 2/2018 | ........... | B60B 19/003 |

OTHER PUBLICATIONS

Korean Notice of Allowance for related KR Application No. 10-2019-0039604 dated Nov. 22, 2020 from Korean Intellectual Property Office.

* cited by examiner

PLASMA SKIN CARE DEVICE

CROSS-REFERENCE TO RELATED APPLICATION

This application claims priority to Korean Patent Application No. 10-2019-0039604 (filed on Apr. 4, 2019), which is hereby incorporated by reference in its entirety.

BACKGROUND

The present invention relates to a plasma skin care device, and more particularly, to a plasma skin care device that allows plasma to be discharged such that ozone which is harmful to a human body and generated during plasma discharge is removed for safety while effects of skin surface modification and performance of cosmetic ingredients are enhanced due to plasma energy.

Recently, as methods for skin regeneration, instead of the existing methods of applying a medicine such as a solution, cream, gel, ointment, or the like to skin, various skin care devices are being used such that negative pressure, ultrasonic waves, or high frequency heat is applied to skin or the skin is stimulated with steam, anion, cold and warm stimulation, vibration stimulation, or the like.

More recently, advanced plasma skin care devices, which are known to have an excellent skin regeneration effect due to plasma without having any problems, such as fever, noise and vibration, skin problems due to allergies, and an increase in volume, of the existing skin care devices, have been developed.

Such a plasma skin care device allows plasma, which is known to have an excellent skin regeneration effect, to not come into direct contact with skin and delivers energy only to tissues in the skin to be treated, and thus the skin's epidermis, which acts as a protective film until new skin is regenerated, may not be damaged. In addition, the plasma skin care device may continuously regenerate the skin, thereby continuously enhancing the effect over time.

Accordingly, it is known that the plasma skin care device has a significant wrinkle improvement effect, tightens the skin, and has comprehensive skin care treatment effects such as skin tone, texture, and pigment enhancement. In addition, it is know that the plasma skin care device may evenly and effectively irradiate a face with plasma energy without pain so that it is possible to smoothly treat curved skin, in particular, skin around a mouth or skin around cheekbones.

However, in the case of the plasma skin care device according to the related art, when a concentration of plasma is increased in a process of discharging the plasma, there is a problem in that ozone, which is known to cause coughing, headaches, asthma, and allergic diseases, is generated.

DOCUMENT OF RELATED ART

Patent Document (Patent Document 1) Korean Patent Registration No. 10-1773847 (Published on Sep. 1, 2017)

SUMMARY

The present invention is directed to providing a plasma skin care device that allows plasma to be discharged such that ozone which is harmful to a human body and generated during plasma discharge is removed for safety while effects of skin surface modification and performance of cosmetic ingredients are enhanced due to plasma energy.

According to an aspect of the present invention, there is provided a plasma skin care device including a handpiece which has a plasma generator and discharges plasma in a state in which a front end portion of the plasma generator is adjacent to skin, an ozone decomposition module configured to receive and decompose ozone, which is generated when the plasma is discharged, from the handpiece, and a suction fan configured to draw the ozone generated in the handpiece to the ozone decomposition module by suction pressure.

The ozone decomposition module may include a photocatalyst filter which is brought into contact with the ozone and an ultraviolet lamp configured to activate photocatalyst by emitting ultraviolet rays to the photocatalyst filter so as to decompose the ozone.

The ozone decomposition module may include a heater configured to heat the ozone so as to instantaneously decompose the ozone.

The ozone decomposition module and the suction fan may be provided inside a casing of a main body of the device, and a rear end portion of the handpiece may be connected to the ozone decomposition module through a connection hose so that the suction pressure generated by the suction fan acts on an inside of the handpiece through the connection hose.

A discharge fan may be provided separately from the suction fan in a lower end portion of the casing of the main body of the device, and when the suction fan suctions and discharges gas which is generated by ozone decomposition in the ozone decomposition module, the discharge fan may once again suction the gas discharged by the suction fan inside the casing of the main body of the device and discharge the gas to the outside.

A mounting groove may be formed in an upper end portion of the casing of the main body of the device so as to allow the handpiece to be mounted on the mounting groove when not in use, the mounting groove may be formed in a front surface of the upper end portion of the casing of the main body of the device so as to allow the handpiece to be fitted into the mounting groove from a front thereof, and a fitting portion having a width smaller than that of other portions may be formed in an upper portion of the mounting groove so that a concave portion formed in a main body of the handpiece in a concave shape is fixedly fitted into the fitting portion.

A lower end portion of the casing of the main body of the device may be provided with a pair of moving wheels, which are each provided at one of left and right sides to allow the main body of the device to be moved while being supported on the ground, and a turning wheel, which is formed to have a size smaller than that of the moving wheel at a middle point of the pair of moving wheels so as to easily change a direction of the casing, and an upper end portion of the casing of the main body of the device may be further provided with a moving handle which allows the main body of the device to be pulled in a state of being inclined backward.

The plasma generator may be formed to have a cylindrical body extending forward in a main body casing of the handpiece having an open front surface so that plasma is discharged from a front end portion of the body of the plasma generator.

The plasma generator may be provided with a plurality of plasma generators.

The plasma may be discharged from one selected from among the plurality of plasma generators.

The plasma generator may be provided with three plasma generators, and the three plasma generators are arranged in a triangular shape.

The plasma generators may be hinge-coupled with a link joint interposed therebetween so that the arrangement of the plasma generators is changeable.

The link joint may have a joint so as to perform a rotating operation.

A guide bracket which supports a rear end portion of any one plasma generator among the plurality of plasma generators in sliding forward or backward may be provided inside the main body casing of the handpiece, and the remaining plasma generators may be sequentially and serially connected to the one plasma generator, which is supported by the guide bracket in being slid forward or backward, using the link joint.

The plasma skin care device may further include a ring-shaped skin contact member which is selectively mountable on an accommodating cup, which is provided in the front end portion of the main body casing of the handpiece to have an open front surface, so as to be pressed against the skin stably regardless of the presence of foreign substance or irregular protrusion of the skin in order to intensively care for a certain area of the skin. The skin contact member may include a ring-shaped main body portion having a fitting groove in a rear surface thereof so as to be fitted along a circumferential portion of a front end portion of the accommodating cup, a double outer wall portion having double outer walls which extend to protrude forward along an inner circumferential portion and an outer circumferential portion of a front end portion of the main body portion so as to be spaced apart from each other and to be brought into contact with the skin, a double inner wall portion having double inner walls which are formed in an inner space formed by the double outer wall portion so as to be spaced apart from each other and to be brought into contact with the skin, and an elastic connecting film configured to elastically support the double inner wall portion in being slid forward or backward with respect to the double outer wall portion. The elastic connecting film may include a thin film portion, which is formed as a thin film having a thickness relatively smaller than that of other portions at a portion adjacent to the double outer wall portion, and a connecting portion which is formed to have a thickness gradually increasing from the thin film portion to the double inner wall portion. When a force acts on the double inner wall portion in a direction in which the double inner wall portion is retracted, the double inner wall portion may rotate about the thin film portion and be bent, and the connecting portion may be bent in an arc shape, which is convex in a rearward direction, and thus the double inner wall portion may be allowed to be retracted, and then, when the force acting on the double inner wall portion disappears, the double inner wall portion may be returned to an initial position thereof by elastic force of the connecting portion.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION

Figure 1:
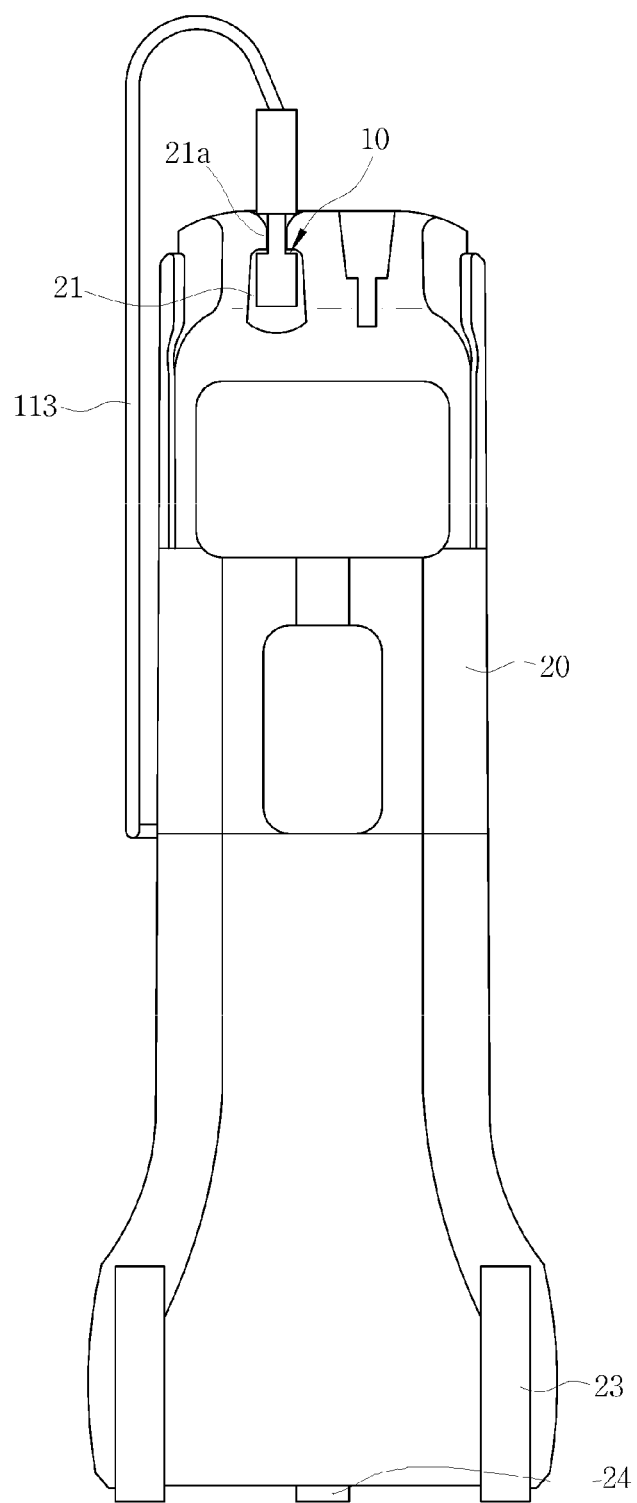
FIG. 1 is a front view of a plasma skin care device according to an embodiment of the present invention.

A plasma skin care device according to embodiments of the present invention will be described in detail with reference to the accompanying drawings. While the present invention is susceptible to various modifications and alternative forms, specific embodiments thereof are shown by way of example in the drawings and will herein be described in detail. It should be understood, however, that there is no intent to limit the present invention to the particular forms disclosed, but on the contrary, the present invention is to cover all modifications, equivalents, and alternatives falling within the spirit and scope of the present invention. Like numbers refer to like elements throughout the description of the drawings. In the accompanying drawings, sizes of structures are illustrated to be larger than actual sizes for clarity of the present invention or to be smaller than the actual sizes for understanding of the schematic configuration.

It will be understood that, although the terms "first," "second," etc. may be used herein to describe various elements, these elements should not be limited by these terms. These terms are only used to distinguish one element from another. For example, a first element could be termed a second element, and, similarly, a second element could be termed a first element without departing from the scope of the present invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

EMBODIMENTS

Figure 2:
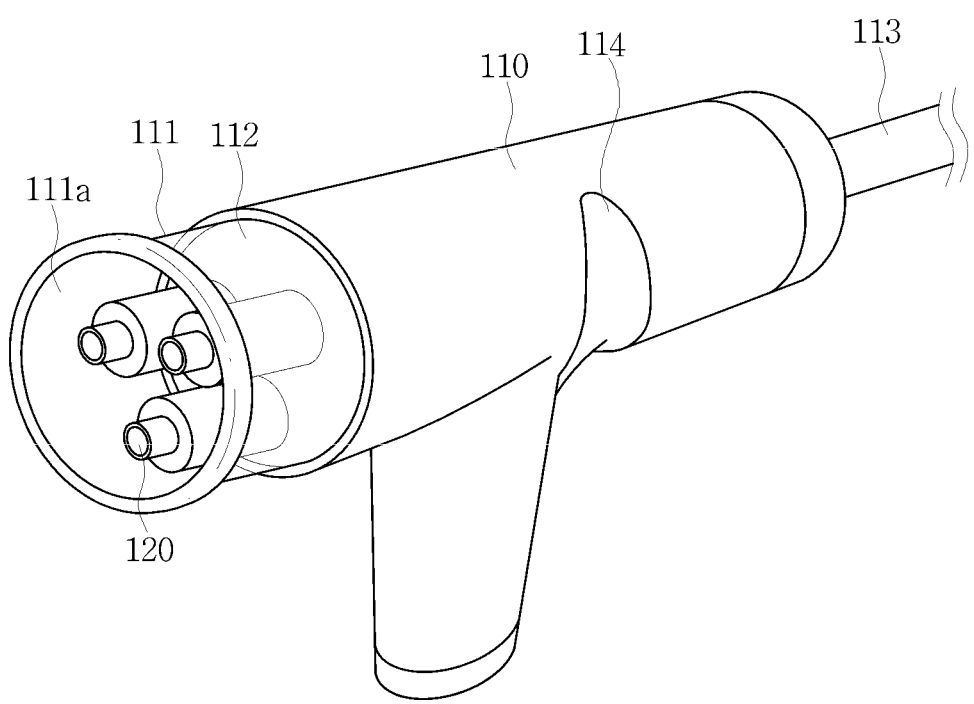
FIG. 2 is a perspective view for describing a handpiece in the plasma skin care device according to the embodiment of the present invention.
Figure 3:
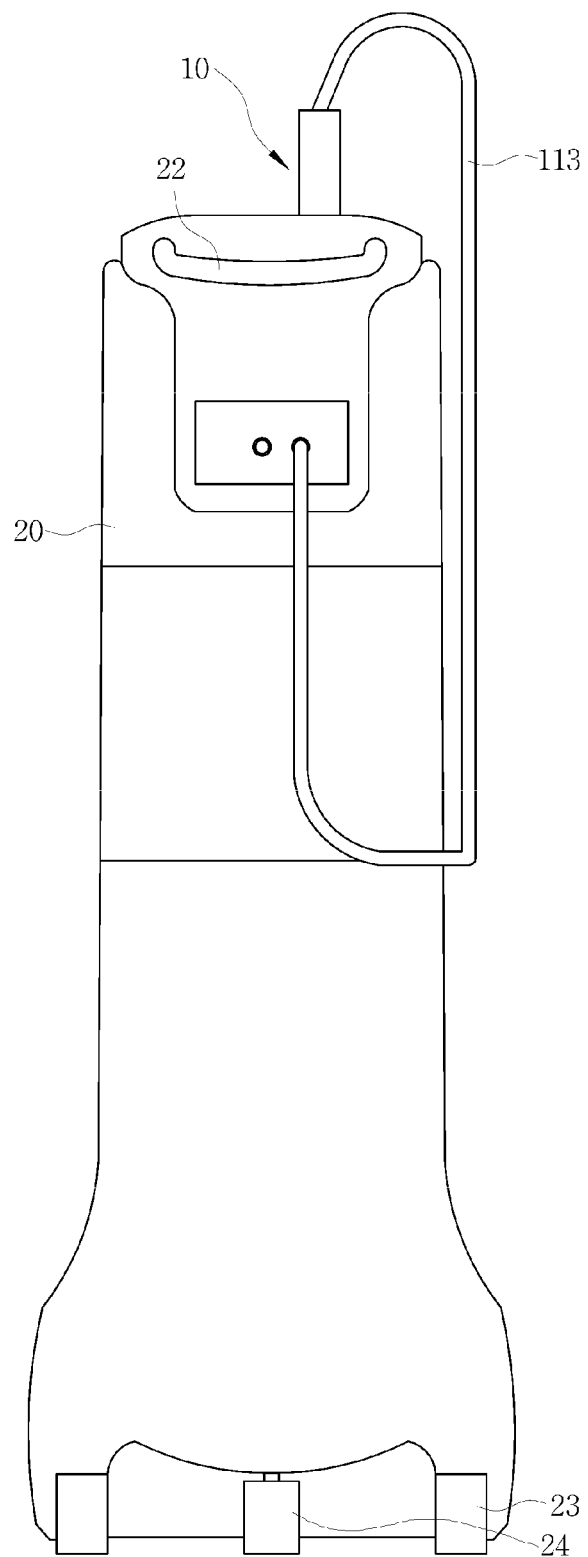
FIG. 3 is a rear view of the plasma skin care device according to the embodiment of the present invention.

FIG. 1 is a front view of a plasma skin care device according to an embodiment of the present invention, and FIG. 2 is a perspective view for describing a handpiece in the plasma skin care device according to the embodiment of the present invention.

As illustrated in the drawings, the plasma skin care device according to the embodiment of the present invention includes a handpiece 10, which is miniaturized to be small enough in size to handle and which generates plasma in a state of being in contact with skin, and includes an ozone decomposition module 30, a suction fan 40, a discharge fan 50, and a gas container 60, which are provided in an inner space 20a of a casing 20 of a main body of the device.

The plasma skin care device of the present invention, which includes the above main components, may be formed to suction and remove ozone, which is harmful to a human body and generated during plasma discharge, for safety while effects of skin surface modification and performance of cosmetic ingredients due to plasma energy are enhanced.

Hereinafter, the components of the plasma skin care device according to the embodiment of the present invention will be mainly described in more detail.

The handpiece 10 includes a plurality of plasma generators 120 that may discharge plasma in a state of being adjacent to skin, as illustrated in FIG. 2. The plasma generators 120 are formed to have a cylindrical body extending forward in an accommodating cup 111 provided at a front end portion of a main body 110 of the handpiece, and plasma is discharged from a front end portion of the body of the plasma generator 120. To this end, a gas supply path, through which a predetermined amount of plasma discharge reaction gas, such as argon, supplied from the gas container 60 is injected per hour in order to discharge the plasma, is formed at the front end portion of the body of the plasma generator 120, and an electrode, a dielectric, and the like for discharging the reaction gas are embedded in the front end of the body of the plasma generator 120. Such a plasma generator 120 may be a non-thermal plasma generator which has low energy under relatively low pressure and can easily generate plasma and in which a temperature of the reaction gas is similar to an atmospheric temperature. Since such a plasma generator 120 is a technology already known in Korean Patent Registration No. 10-1773847 (Published on Aug. 28, 2017), a detailed description thereof will be omitted.

As illustrated in FIG. 2, the plasma generators 120 may be accommodated in a main body 110 casing of the handpiece 10 and in a chamber 111a of an accommodating cup 111 having an open front surface in the form of an array in which three plasma generators 120 are arranged in a triangular shape. As described above, when three plasma generators 120 are intensively provided in the form of an array of a triangular shape, the plasma generators 120 may be particularly useful when intensive care is required for a certain area of the skin.

Figure 6:
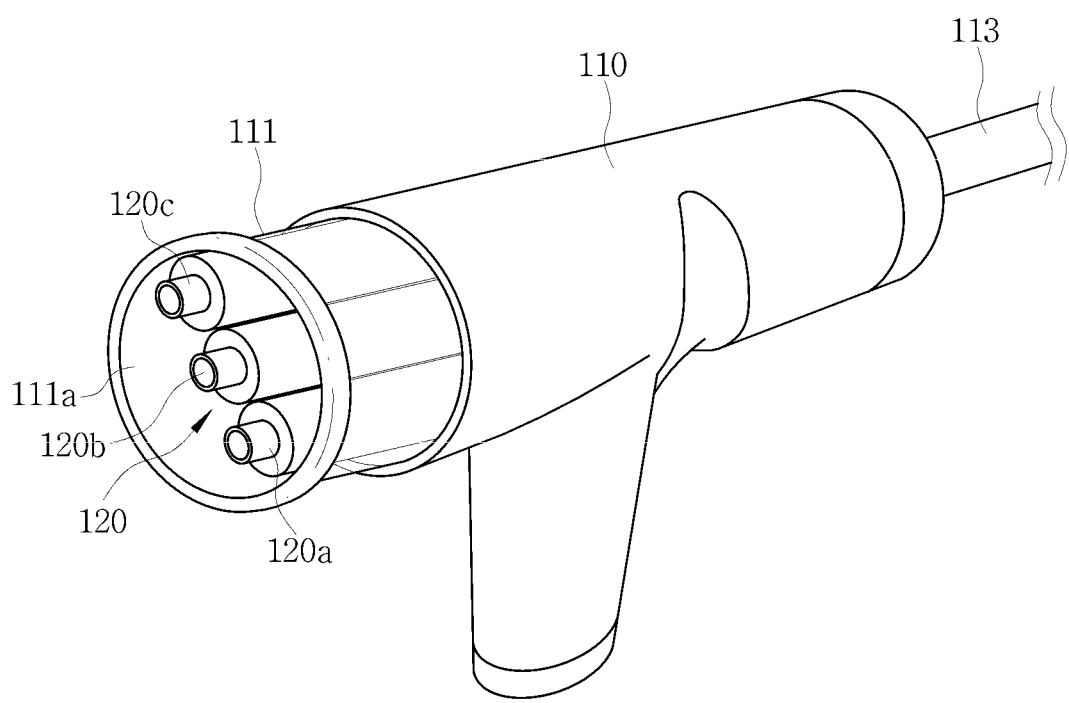
FIG. 6 is a perspective view of a state in which an arrangement of plasma generators is changed in the handpiece of the plasma skin care device according to the embodiment of the present invention.
Figure 7:
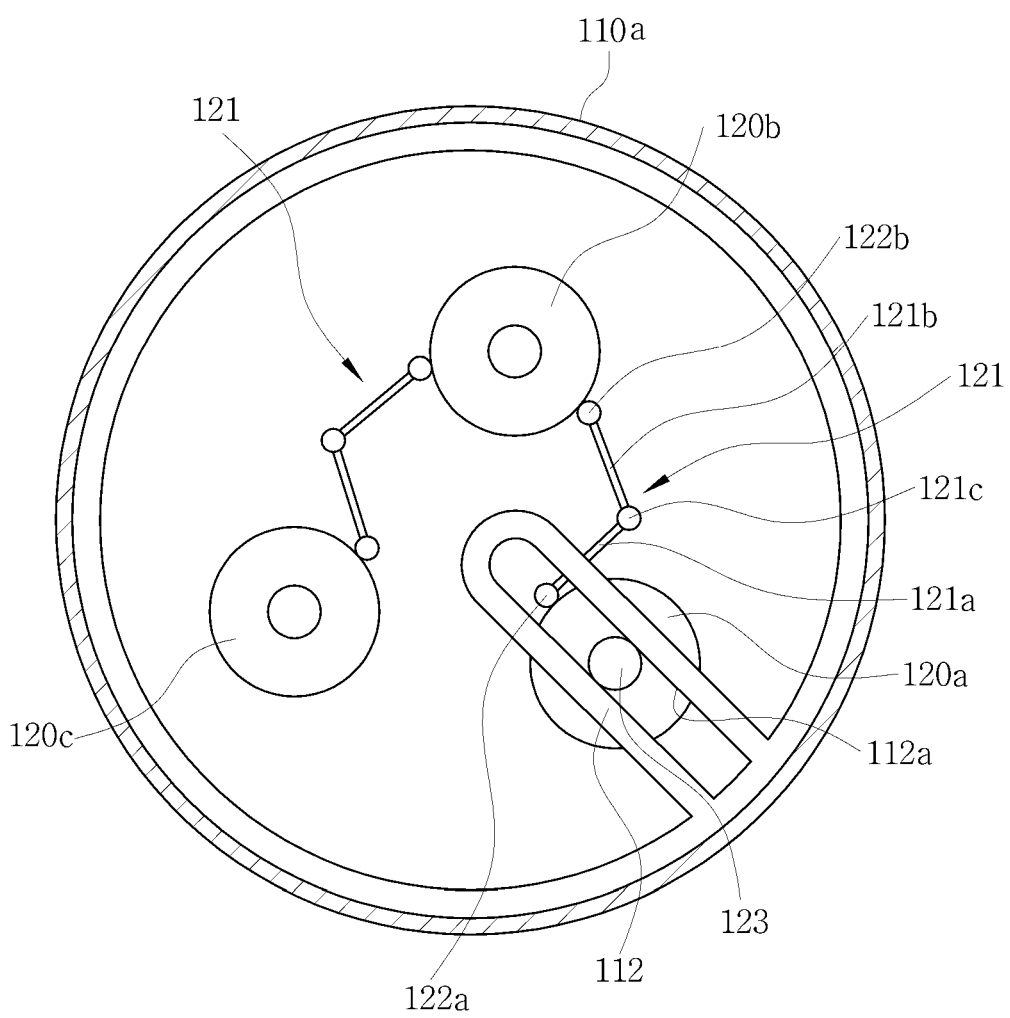
FIGS. 7 and 8 are cross-sectional views for describing a configuration for changing the arrangement of the plasma generators in the handpiece of the plasma skin care device according to the embodiment of the present invention.
Figure 8:
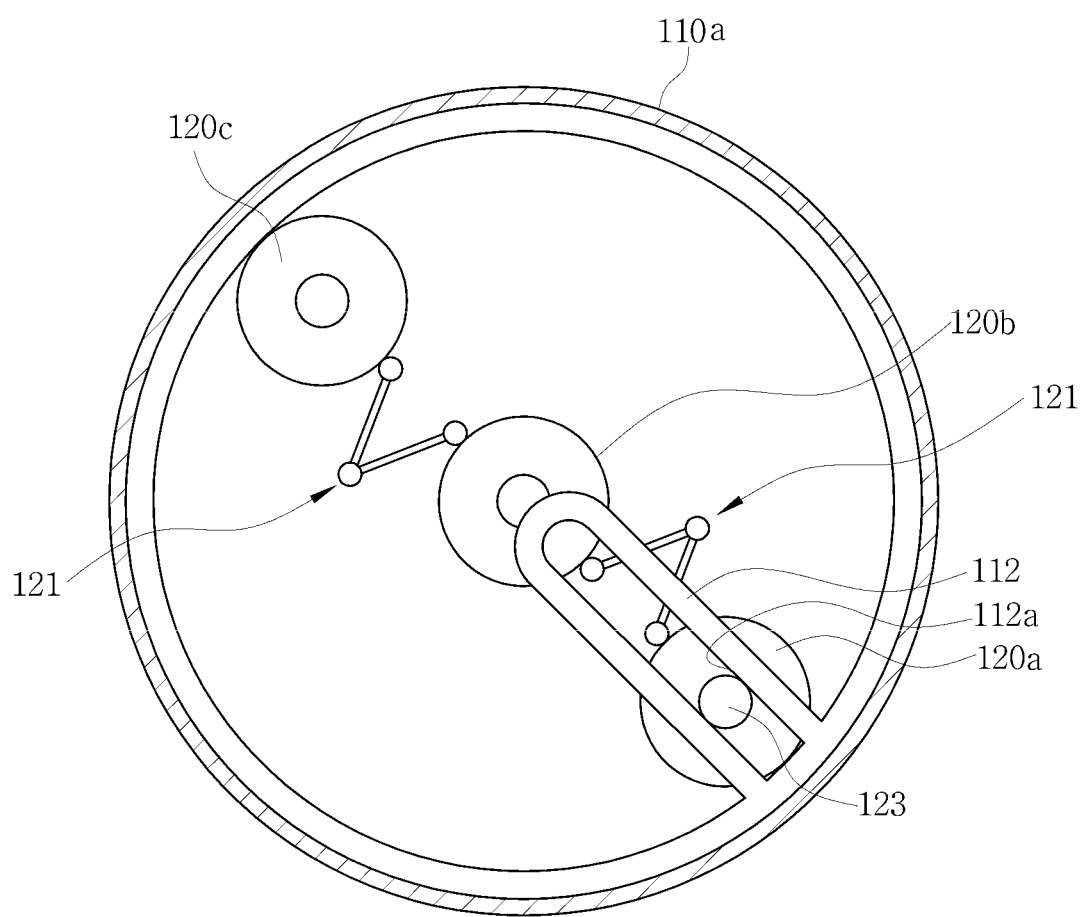

Furthermore, in the present invention, the arrangement of the plasma generators 120 may be freely changed, as illustrated in FIG. 6. To this end, as illustrated in FIGS. 7 and 8, a guide bracket 112 which supports a rear end portion of any one plasma generator 120a among the plurality of plasma generators 120 in sliding forward or backward is provided in the main body 110 casing of the handpiece 10, and the remaining plasma generators 120b and 120c are sequentially and serially connected to the one plasma generator 120a among the plasma generators 120, which is supported by the guide bracket 112 in being slid forward or backward, using link joints 121. The one plasma generator 120a among the plasma generators 120, which is supported in being slid forward or backward, includes a slide protrusion 123 which is slidably fitted to a slide long hole 112a of the guide bracket 112 at the rear end portion thereof, and a power line is connected thereto through the slide protrusion 123. An end portion of each of the link joints 121 interposed between the plasma generators 120 is hinge-coupled using a hinge shaft 122a with respect to the plasma generator 120. Here, the link joint 121 has a joint 121c provided in the middle thereof so as to perform a rotating operation. Therefore, the link joint 121 is formed by coupling two short link joints 121a and 121b to be rotatable about the joint 121c interposed therebetween.

According to the above configuration, the one plasma generator 120a among the plurality of plasma generators 120 may be slid forward or backward in a radial direction of the main body 110 casing of the handpiece 10 along the slide long hole 112a of the guide bracket 112 and positions of the remaining plasma generators 120b and 120c among the plasma generators 120 may be relatively freely changed, and thus the arrangement of the plasma generators 120 may be changed from a triangular form to a one-line form, as illustrated in FIGS. 6 and 8, and may be changed to various forms. Therefore, it is possible to flexibly care for the skin according to the skin condition of a subject.

Preferably, the plurality of plasma generators 120 may be provided to selectively supply power so that not all of the plasma generators 120 discharge plasma and only one or two of the plasma generators 120 selectively discharge plasma. The above configuration also greatly aids in flexibly caring for the skin according to the skin condition of the subject.

The main body 110 of the handpiece may have a concave portion 114 formed in a concave shape and the concave portion 114 may be fixedly fitted into a fitting portion 21a of a mounting groove 21 formed in an upper end portion of the casing 20 of the main body of the device. Preferably, the handpiece 10 may be provided in a gun type so as to facilitate convenient use in a state of simply grasping the handpiece 10.

Figure 4:
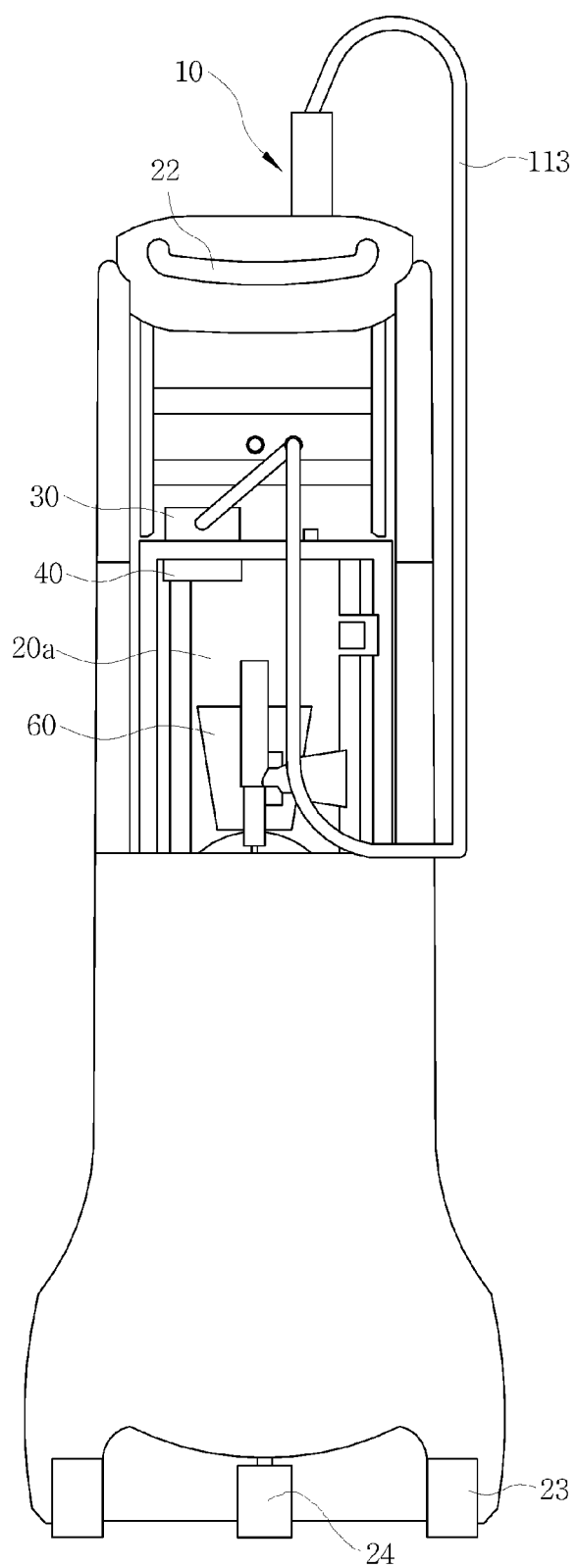
FIG. 4 is a rear view of the plasma skin care device according to the embodiment of the present invention from which an upper portion of a casing of a main body of the device is removed.

The ozone decomposition module 30 is provided in the inner space 20a of the casing 20 of the main body of the device, as illustrated in FIG. 4, and serves to receive and decompose ozone, which is generated when the plasma is discharged, from the handpiece 10. To this end, the ozone decomposition module 30 may use any one of photocatalytic and pyrolysis methods that are already well known as ozone decomposition methods. When the ozone decomposition module 30 uses the photocatalyst method, a sealed module case includes a photocatalyst filter which is in contact with the ozone and an ultraviolet lamp which activates photocatalyst by emitting ultraviolet rays to the photocatalyst filter. When the ozone decomposition module 30 uses the pyrolysis method, the sealed module case includes a heater that can provide high temperature heat so as to instantaneously decompose the ozone by heating the received ozone.

Here, in order to allow the ozone generated in the handpiece 10 to be transmitted to the ozone decomposition module 30 without leakage, a rear end portion of the main body 110 of the handpiece is connected to the module case of the ozone decomposition module 30 through a flexible connection hose 113. The connection hose 113 connects the handpiece 10 to the ozone decomposition module 30 in a state of passing through a rear surface of the casing 20 of the main body of the device.

The suction fan 40 serves to draw the ozone generated in the handpiece 10 to the ozone decomposition module 30 by suction pressure, as illustrated in FIG. 4. To this end, the suction fan 40 is disposed opposite to the handpiece 10 with the ozone decomposition module 30 interposed therebetween in consideration of the arrangement according to the flow of the ozone. In FIG. 4, the suction fan 40 is illustrated as being provided below the ozone decomposition module 30.

Figure 5:
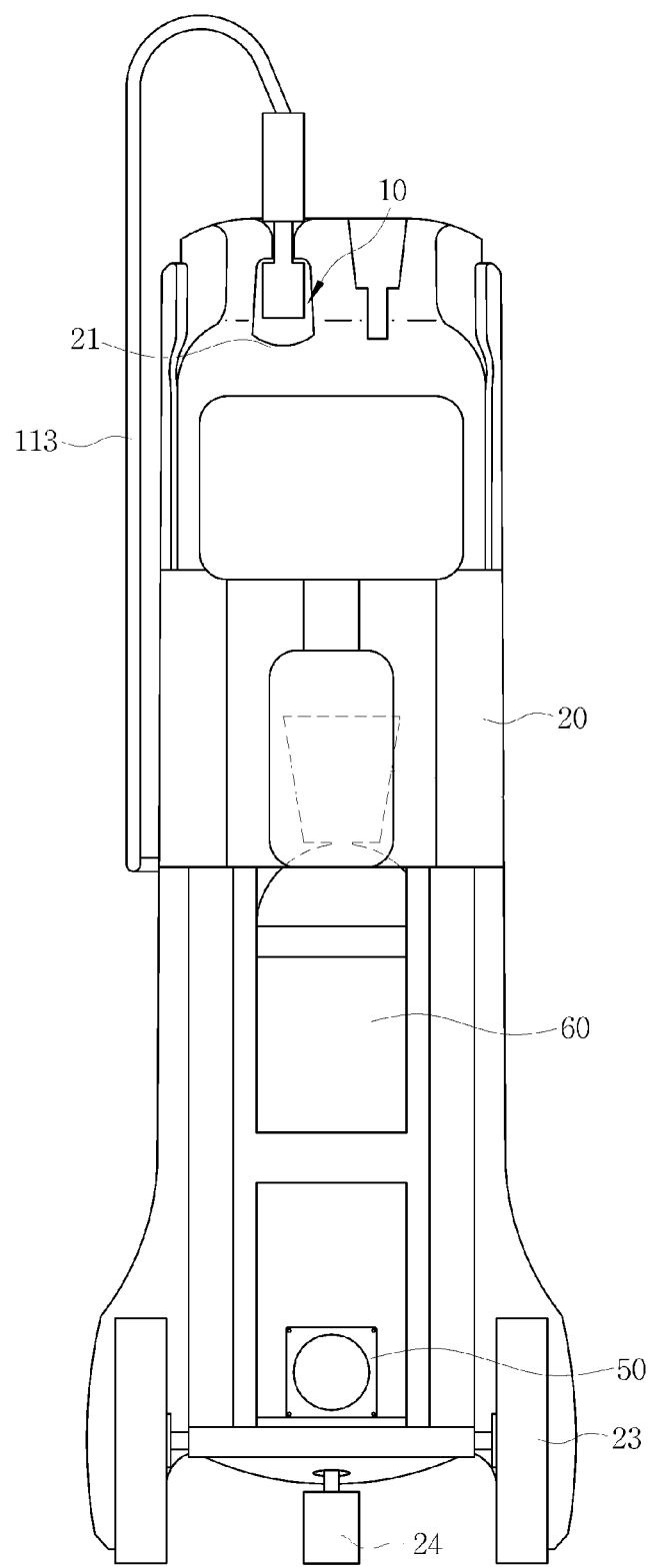
FIG. 5 is a front view of the plasma skin care device according to the embodiment of the present invention from which a lower portion of the casing of the main body of the device is removed.

A discharge fan 50 is provided separately from the suction fan 40 in a lower end portion of the casing 20 of the main body of the device, as illustrated in FIG. 5. As a result, when the suction fan 40 suctions and discharges gas which is generated by ozone decomposition in the ozone decomposition module 30, the discharge fan 50 once again suctions the gas discharged by the suction fan 40 inside the inner space 20a of the casing 20 of the main body of the device and discharges the gas to the outside. According to the configuration in which a separate discharge fan 50 is provided in addition to the suction fan 40, the entire flow of ozone and decomposed gas occurring while suctioning and decomposing the ozone and discharging the decomposed gas to the outside is performed very smoothly. However, when the discharge fan 50 is excluded and only the suction fan 40 is provided, the gas generated by ozone decomposition may not be completely discharged from the inside of the main body of the device and may remain therein, thereby obstructing the entire flow of ozone and decomposed gas.

A pair of moving wheels 23, which are each provided at one of left and right sides to allow the main body of the device to be moved while being supported on the ground, are provided in the lower end portion of the casing 20 of the main body of the device. In addition, a turning wheel (24) is provided to have a size smaller than that of the moving wheel 23 at a middle point of the pair of moving wheels 23 so as to easily change a direction of the casing 20. In conjunction with the moving wheels 23 and the turning wheel 24, a moving handle 22 may be provided in the upper end portion of the casing 20 of the main body of the device and thus may allow the main body of the device to be pulled in a state of being inclined backward.

Figure 9:
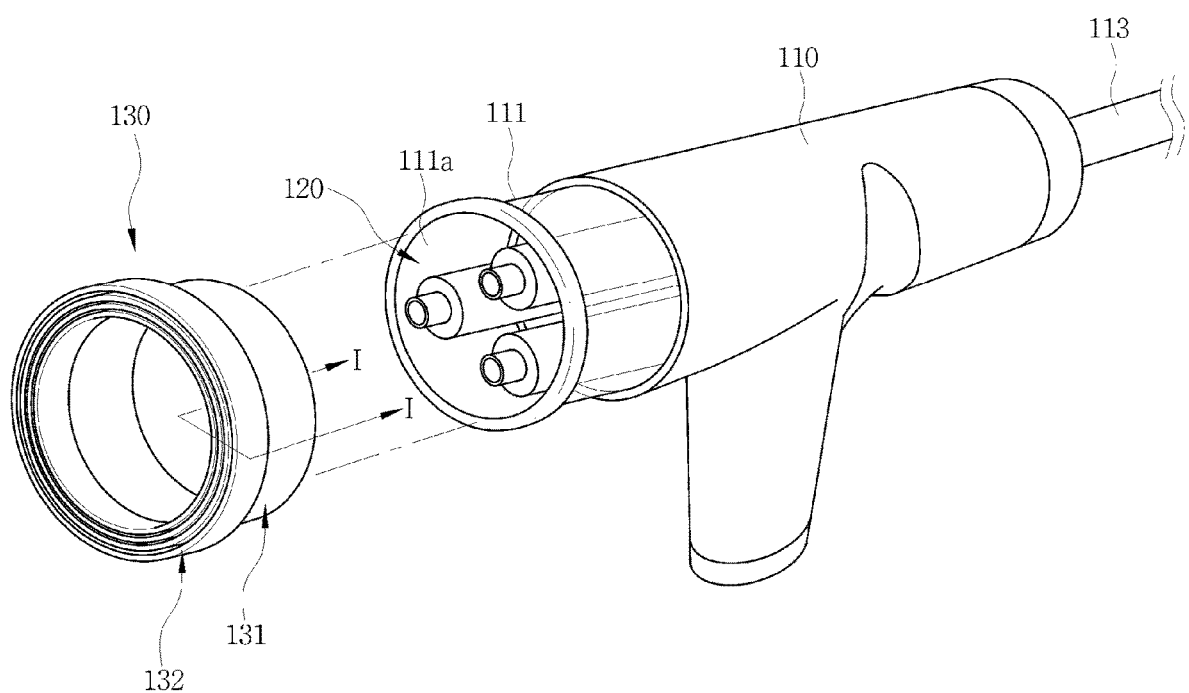
FIG. 9 is a perspective view for describing a skin contact member selectively mounted in the plasma skin care device according to the embodiment of the present invention.
Figure 10:
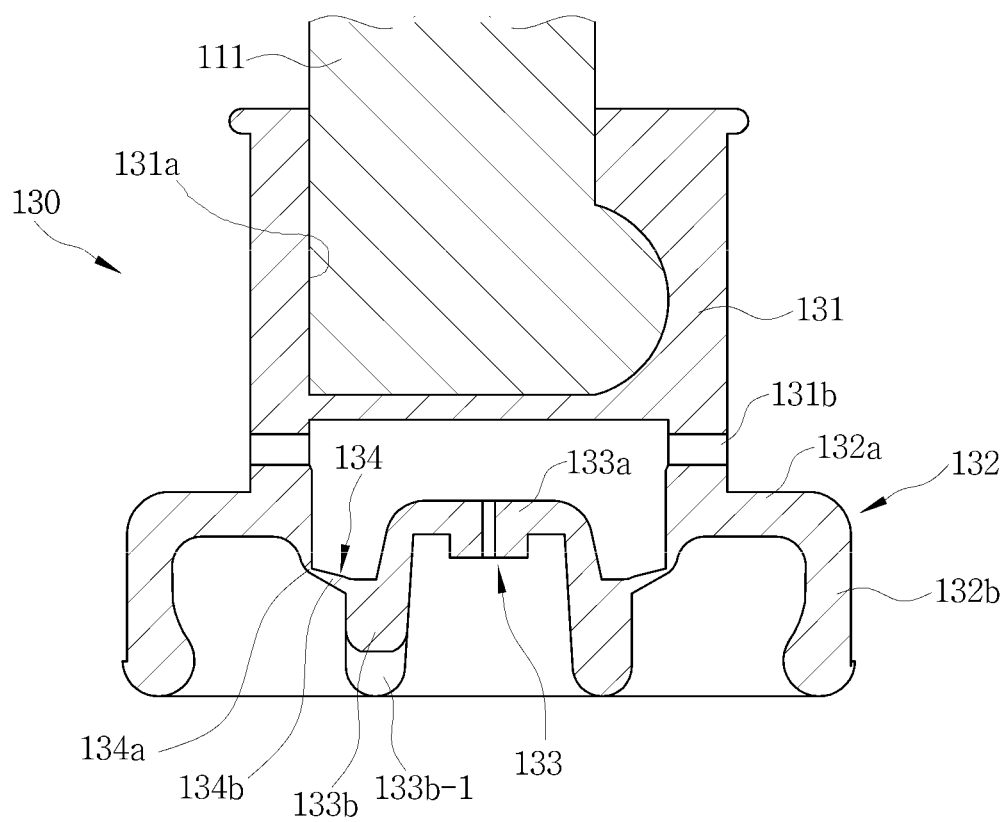
FIG. 10 is a cross-sectional view of the skin contact member taken along line I-I of FIG. 9.

FIG. 9 is a perspective view for describing a skin contact member selectively mounted in the plasma skin care device according to the embodiment of the present invention, FIG. 10 is a cross-sectional view of the skin contact member taken along line I-I of FIG. 9, and FIGS. 11 to 13 are a series of reference diagrams for describing performance and operation of the skin contact member in the plasma skin care device according to the embodiment of the present invention.

As illustrated in the drawings, in order to intensively care for a certain area of the skin, the plasma skin care device further includes a ring-shaped skin contact member 130 which is selectively mountable on the accommodating cup 111 of the handpiece 10 so as to press against the skin stably regardless of the presence of a foreign substance or an irregular protrusion of the skin. The skin contact member 130 may be made of a soft elastic material such as urethane or rubber and may include a main body portion 131, a double outer wall portion 132, a double inner wall portion 133, and an elastic connecting film 134, which are integrally molded.

The main body portion 131 has a fitting groove 131a provided in a rear surface thereof so as to be fitted along a circumferential portion of a front end portion of the accommodating cup 111 and is formed in a ring shape. The double outer wall portion 132 is provided with double outer walls 132b which extend to protrude forward along an inner circumferential portion and an outer circumferential portion of a front end portion of the main body portion 131 so as to be spaced apart from each other and to be brought into contact with the skin. The double inner wall portion 133 is provided with double inner walls 133b which are formed in an inner space formed by the double outer wall portion 132 so as to be spaced apart from each other and to be brought into contact with the skin. The double inner walls 133b of the double inner wall portion 133 are connected to each other by a bridge portion 133a. Meanwhile, the elastic connecting film 134 elastically supports the double inner wall portion 133 in being slid forward or backward with respect to the double outer wall portion 132.

Here, a detailed configuration of the elastic connecting film 134 will be described. The elastic connecting film 134 includes a thin film portion 134a, which is formed as a thin film having a thickness relatively smaller than that of other portions at a portion adjacent to the double outer wall portion 132, and a connecting portion 134b which is formed to have a thickness gradually increasing from the thin film portion 134a to the double inner wall portion 133. According to such a configuration of the elastic connecting film 134, as illustrated in a series of processes illustrated in FIGS. 11 to 13, when a force acts on the double inner wall portion in a direction in which the double inner wall portion 133 is retracted, due to foreign matter or irregularly protruding skin OB, the double inner wall portion 133 rotates about the thin film portion 134a and is bent, and the connecting portion 134b is bent in an arc shape, which is convex in a rearward direction, and thus the double inner wall portion 133 is allowed to be retracted. Thereafter, when the force acting on the double inner wall portion 133 disappears, the double inner wall portion 133 is returned to an initial position thereof by elastic force of the connecting portion 134b.

Figure 11:
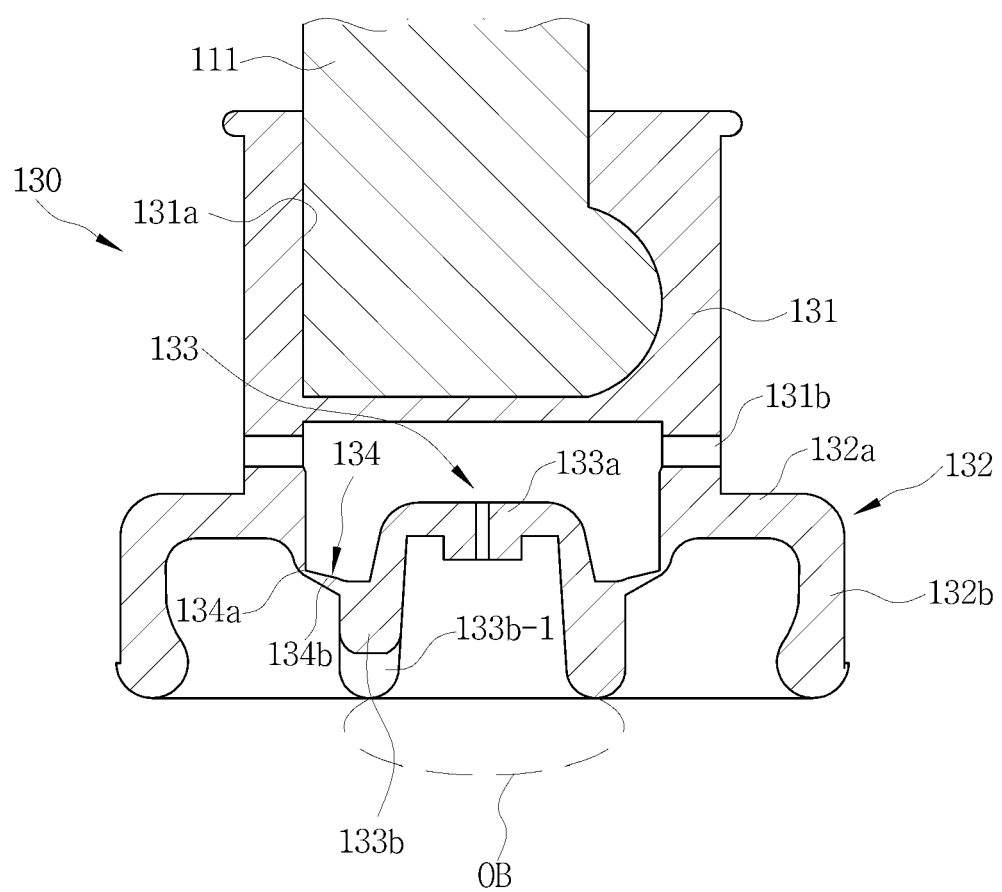
FIGS. 11 to 13 are a series of reference diagrams for describing performance and operation of the skin contact member in the plasma skin care device according to the embodiment of the present invention.
Figure 12:
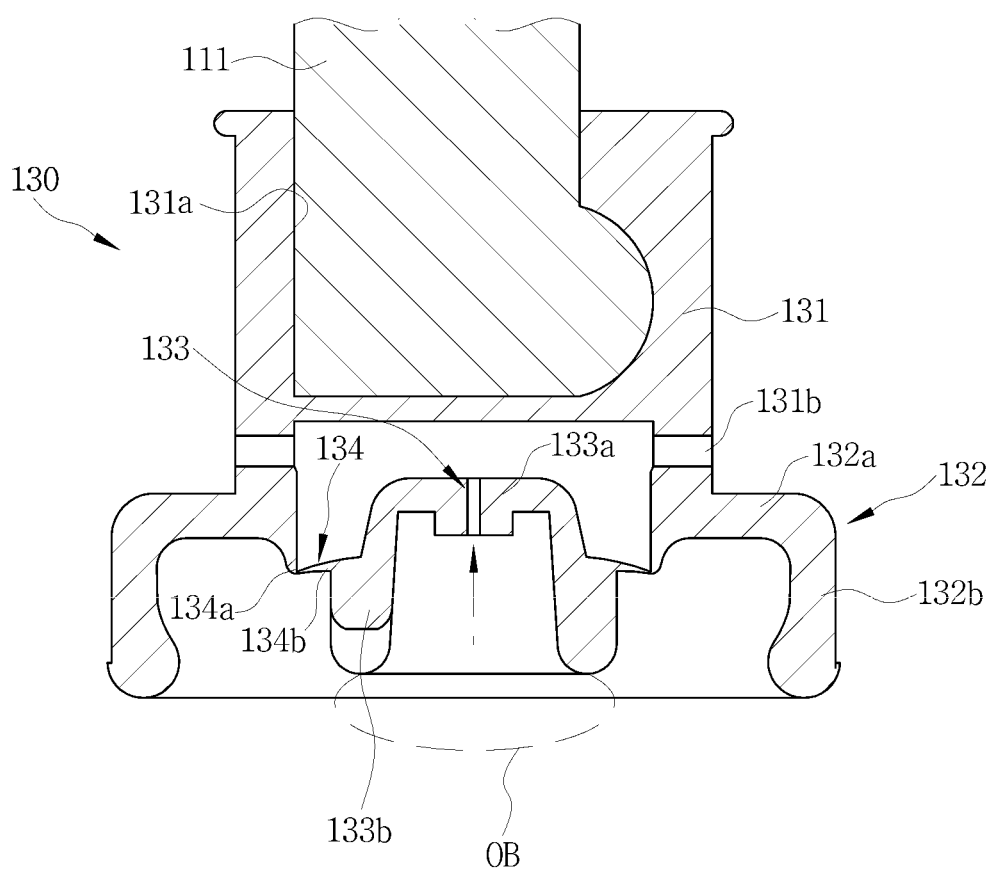
Figure 13:
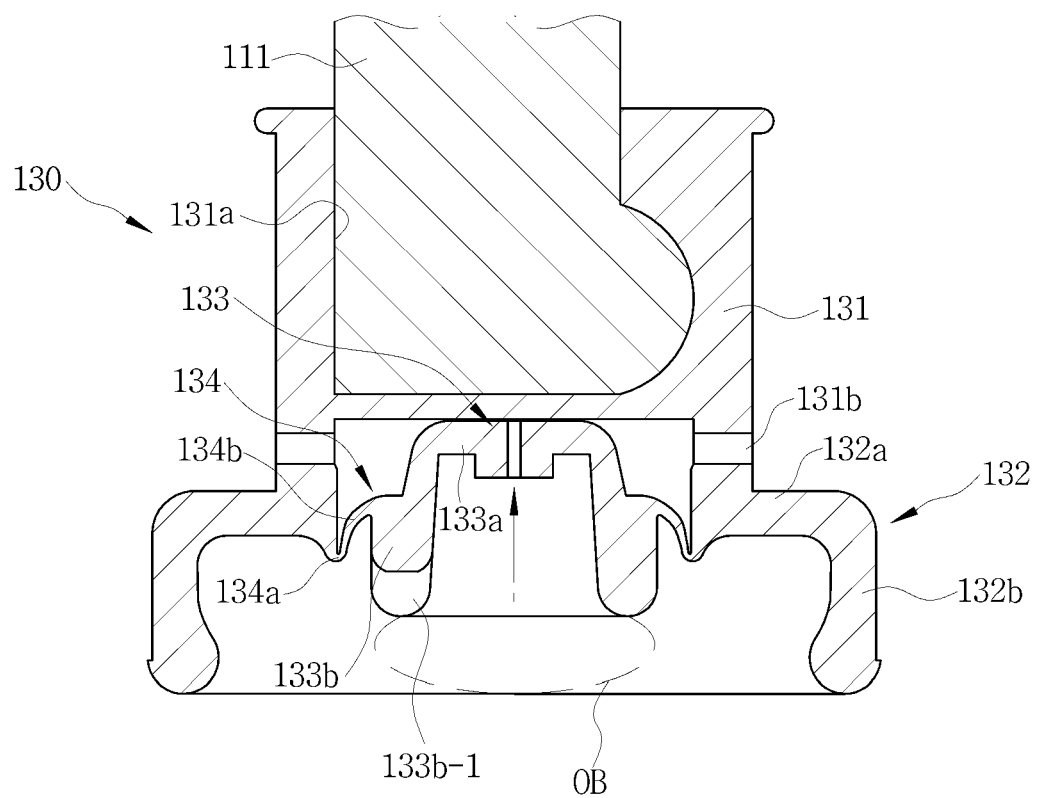

According to a configuration in which such a skin contact member 130 is provided, as illustrated in the drawings, ordinarily, a quadruple multi-wall may be formed by the double inner wall portion 133 and the double outer wall portion 132 so as to be brought into contact with the skin stably. Even when irregularly protruding skin OB or foreign substance is present as illustrated in FIGS. 11 to 13, at least a double wall may be formed to maintain a stable state while in contact with the skin. As a result, the plasma may be discharged in a state in which the handpiece 10 is pressed against the skin very stably.

Here, an air circulation hole 131b formed in the main body portion 131 of the skin contact member 130 may allow external air to be introduced and thus may allow ozone to be smoothly moved toward the ozone decomposition module 30 when a suction force acts by the suction fan 40. A communication groove 133b-1 formed in the double inner wall portion 133 partially allows air or gas to flow and suppresses the formation of a vacuum pressure in a space surrounded by the double outer wall portion 132 and the double inner wall portion 133.

According to the present invention, the plasma skin care device can discharge plasma such that ozone which is harmful to a human body and generated during plasma discharge is removed for safety while effects of skin surface modification and performance of cosmetic ingredients are enhanced due to plasma energy.

Further, in the plasma skin care device of the present invention, an arrangement of a plurality of plasma generators can be changed so that plasma can be discharged while the arrangement is appropriately changed according to the situation.

Although the exemplary embodiments of the present invention have been described, the present invention may use various changes, modifications, and equivalents. It is clear that the present invention can be applied in the same manner by appropriately modifying the above embodiments. Therefore, the above description does not limit the scope of the present invention as defined by the limitations of the following claims.

What is claimed is:

1. A plasma skin care device comprising:
a handpiece which has a plasma generator and discharges plasma in a state in which a front end portion of the plasma generator is adjacent to skin;
an ozone decomposition module configured to receive and decompose ozone, which is generated when the plasma is discharged, from the handpiece; and
a suction fan configured to draw the ozone generated in the handpiece to the ozone decomposition module by suction pressure,
wherein the plasma generator is formed to have a cylindrical body extending forward in a main body casing of the handpiece having an open front surface so that plasma is discharged from a front end portion of the body of the plasma generator,
wherein the plasma skin care device further comprises:
a ring-shaped skin contact member which is selectively mountable on an accommodating cup, which is provided in the front end portion of the main body casing of the handpiece to have an open front surface, so as to be pressed against the skin stably regardless of the presence of foreign substance or irregular protrusion of the skin in order to intensively care for a certain area of the skin,
wherein the skin contact member includes:
a ring-shaped main body portion having a fitting groove in a rear surface thereof so as to be fitted along a circumferential portion of a front end portion of the accommodating cup;
a double outer wall portion having double outer walls which extend to protrude forward along an inner circumferential portion and an outer circumferential portion of a front end portion of the main body portion so as to be spaced apart from each other and to be brought into contact with the skin;
a double inner wall portion having double inner walls which are formed in an inner space formed by the double outer wall portion so as to be spaced apart from each other and to be brought into contact with the skin; and
an elastic connecting film configured to elastically support the double inner wall portion in being slid forward or backward with respect to the double outer wall portion,
the elastic connecting film includes a thin film portion, which is formed as a thin film having a thickness relatively smaller than that of other portions at a portion adjacent to the double outer wall portion, and a connecting portion which is formed to have a thickness gradually increasing from the thin film portion to the double inner wall portion, and
when a force acts on the double inner wall portion in a direction in which the double inner wall portion is retracted, the double inner wall portion rotates about the thin film portion and is bent, and the connecting portion is bent in an arc shape, which is convex in a rearward direction, and thus the double inner wall portion is allowed to be retracted, and then, when the force acting on the double inner wall portion disappears, the double inner wall portion is returned to an initial position thereof by elastic force of the connecting portion.

2. The plasma skin care device of claim 1, wherein the ozone decomposition module includes a photocatalyst filter which is brought into contact with the ozone and an ultraviolet lamp configured to activate photocatalyst by emitting ultraviolet rays to the photocatalyst filter so as to decompose the ozone.

3. The plasma skin care device of claim 1, wherein the ozone decomposition module includes a heater configured to heat the ozone so as to instantaneously decompose the ozone.

4. The plasma skin care device of claim 1, wherein the ozone decomposition module and the suction fan are provided inside a casing of a main body of the device, and a rear end portion of the handpiece is connected to the ozone decomposition module through a connection hose so that the suction pressure generated by the suction fan acts on an inside of the handpiece through the connection hose.

5. The plasma skin care device of claim 4, wherein a discharge fan is provided separately from the suction fan in a lower end portion of the casing of the main body of the device and, when the suction fan suctions and discharges gas which is generated by ozone decomposition in the ozone decomposition module, the discharge fan once again suctions the gas discharged by the suction fan inside the casing of the main body of the device and discharges the gas to the outside.

6. The plasma skin care device of claim 4, wherein:
a mounting groove is formed in an upper end portion of the casing of the main body of the device so as to allow the handpiece to be mounted on the mounting groove when not in use; and
the mounting groove is formed in a front surface of the upper end portion of the casing of the main body of the device so as to allow the handpiece to be fitted into the mounting groove from a front thereof, and a fitting portion having a width smaller than that of other portions is formed in an upper portion of the mounting groove so that a concave portion formed in a main body of the handpiece in a concave shape is fixedly fitted into the fitting portion.

7. The plasma skin care device of claim 4, wherein:
a lower end portion of the casing of the main body of the device is provided with a pair of moving wheels, which are each provided at one of left and right sides to allow the main body of the device to be moved while being supported on the ground, and a turning wheel which is formed to have a size smaller than that of the moving wheel at a middle point of the pair of moving wheels so as to easily change a direction of the casing; and
an upper end portion of the casing of the main body of the device is further provided with a moving handle which allows the main body of the device to be pulled in a state of being inclined backward.

8. The plasma skin care device of claim 1, wherein the plasma generator is provided with a plurality of plasma generators.

9. The plasma skin care device of claim 8, wherein the plasma is discharged from one selected from among the plurality of plasma generators.

10. The plasma skin care device of claim 8, wherein the plasma generator is provided with three plasma generators, and the three plasma generators are arranged in a triangular shape.

11. A plasma skin care device comprising:
- a handpiece which has a plasma generator and discharges plasma in a state in which a front end portion of the plasma generator is adjacent to skin;
- an ozone decomposition module configured to receive and decompose ozone, which is generated when the plasma is discharged, from the handpiece; and
- a suction fan configured to draw the ozone generated in the handpiece to the ozone decomposition module by suction pressure,
- wherein the plasma generator is formed to have a cylindrical body extending forward in a main body casing of the handpiece having an open front surface so that plasma is discharged from a front end portion of the body of the plasma generator,
- wherein the plasma generator is provided with a plurality of plasma generators, and
- wherein the plasma generators are hinge-coupled with a link joint interposed therebetween so that the arrangement of the plasma generators is changeable.

12. The plasma skin care device of claim 11, wherein the link joint has a joint so as to perform a rotating operation.

13. The plasma skin care device of claim 12, wherein a guide bracket which supports a rear end portion of any one plasma generator among the plurality of plasma generators in sliding forward or backward is provided inside the main body casing of the handpiece, and the remaining plasma generators are sequentially and serially connected to the one plasma generator, which is supported by the guide bracket in being slid forward or backward, using the link joint.

* * * * *